United States Patent [19]

Carter

[11] 4,374,199
[45] Feb. 15, 1983

[54] METHOD FOR GENERATION OF BIO-GAS

[76] Inventor: Vernon H. Carter, P.O. Box 95 PSR, Elkins, Ark. 72727

[21] Appl. No.: 203,247

[22] Filed: Nov. 3, 1980

[51] Int. Cl.³ .................. C05F 11/08; C12N 13/00; C12P 5/02
[52] U.S. Cl. .................. 435/167; 435/170; 435/173; 435/813; 210/603; 48/197 A; 71/10
[58] Field of Search ............ 435/167, 170, 173, 299, 435/317, 813, 253, 822; 426/55, 56, 59; 48/197 A; 210/603; 71/8, 9, 10

[56] References Cited

U.S. PATENT DOCUMENTS

| | | | |
|---|---|---|---|
| 3,336,220 | 8/1967 | Neidl | 435/173 |
| 3,871,961 | 3/1975 | Gianessi | 435/173 |
| 3,973,043 | 8/1976 | Lynn | 426/55 |
| 4,100,023 | 7/1978 | McDonald | 435/167 |
| 4,152,210 | 5/1979 | Robinson et al. | 435/173 |

OTHER PUBLICATIONS

Kalmijn, A. J. et al., "The Magnetic Behavior of Mud Bacteria," *Animal Migration, Navigation and Homing*, Schmidt-Koenig et al. eds., 1978, pp. 344-345.
Blakemore, R. P. et al., *Nature*, vol. 286, Jul. 1980, pp. 384-385.
Schlegel, H. G. et al., *Microbial Energy Conversion*, Pergamon Press, 1977; pp. 107-108.

*Primary Examiner*—Raymond N. Jones
*Assistant Examiner*—Elizabeth J. Curtin
*Attorney, Agent, or Firm*—Boyd D. Cox

[57] ABSTRACT

Improved method for the production of bio-gas incorporating a magnetic field to situate magnetotactic bacteria in the reactive zone of a bio-gas producing digester.

6 Claims, 1 Drawing Figure

METHOD FOR GENERATION OF BIO-GAS

FIELD OF THE INVENTION

This invention relates to bio-gas production and more particularly to a method for producing bio-gas more efficiently through the use of magnetotactic bacteria.

BACKGROUND OF THE INVENTION

According to recent reports, two billion tons of organic waste per year are available on United States farms. These organic wastes can readily be converted to a methane containing gas, or bio-gas, by fermentation of the wastes in a digester. One such process is disclosed in U.S. Pat. No. 3,973,043.

It has been determined that one ton of manure will produce approximately two thousand cubic feet of bio-gas. Therefore, approximately four thousand billion cubic feet of bio-gas could be produced per year in the United States. Since two hundred twenty cubic feet of bio-gas is approximately equivalent to one gallon of gasoline, approximately nine gallons of gasoline could be recovered from one ton of manure, or approximately eighteen billion gallons from two billion tons.

In terms of electrical energy, since twenty cubic feet of bio-gas is approximately equivalent to one Kilo Volt Ampere (K.V.A.), approximately two hundred billion K.V.A.'s could be generated per year.

Obviously, there is great energy generation potential through this type conversion. However, to data the economics of operation to produce bio-gas have not been favorable enough to make bio-gas production readily acceptable. As a consequence, several means for optimizing this type production have been proposed. One such means is disclosed in U.S. Pat. No. 4,100,023. Another is disclosed in the co-pending application of Carter entitled "Improved Bio-Gas Generating Digester," Ser. No. 187,466, filed Sept. 15, 1980.

Accordingly, one object of the present invention is the provision of a more efficient means of producing bio-gas by preventing the loss of bacteria from the digester as sludge is withdrawn therefrom.

Another object of the present invention is the provision of a more efficient means of producing bio-gas by situating bacteria in the zone of the digester where the bacteria will be the most productive.

Still another object of the present invention is the provision of a more efficient means of producing bio-gas by increasing the flow rate of material through the digester.

SUMMARY OF THE INVENTION

In practice, bio-gas is normally produced in a digester by the fermentation of organic wastes. Often bacteria is added to the organic wastes to facilitate the fermentation therof. The particular bacteria chosen for addition varies depending on the composition of the organic wastes.

Although bacteria addition can be beneficial in producing bio-gas, certain processing problems are commonly encountered when bacteria are added to the organic wastes. First of all, bacteria become entrapped in sludge which is formed in the digester and are lost as the sludge is withdrawn from the digester. This loss becomes greater as the flow rate of material through the digester is increased. One way to reduce this loss is to reduce such flow rate, but, of course, this reduces the amount of organic wastes that can be processed in a given time period.

A better way to reduce the loss of bacteria from the digester is to initially use magnetotactic (magnetically sensitive) bacteria and prohibit bacteria from exiting the digester with the sludge by creating a magnetic field to situate bacteria apart from the sludge. Since the bacteria can be kept apart from the sludge by utilizing such a magnetic field, sludge can be withdrawn from the digester at a more rapid rate and more organic wastes processed in a given time period.

Furthermore, by properly positioning the magnetic field the magnetotactic bacteria can be made to occupy the area of the digester where they will be most productive and thereby make the entire bio-gas generation operation more efficient.

Other objects, features and advantages of the present invention will become apparent from a consideration of the following detailed description and from the accompanying drawing.

DETAILED DESCRIPTION

Figure 1:
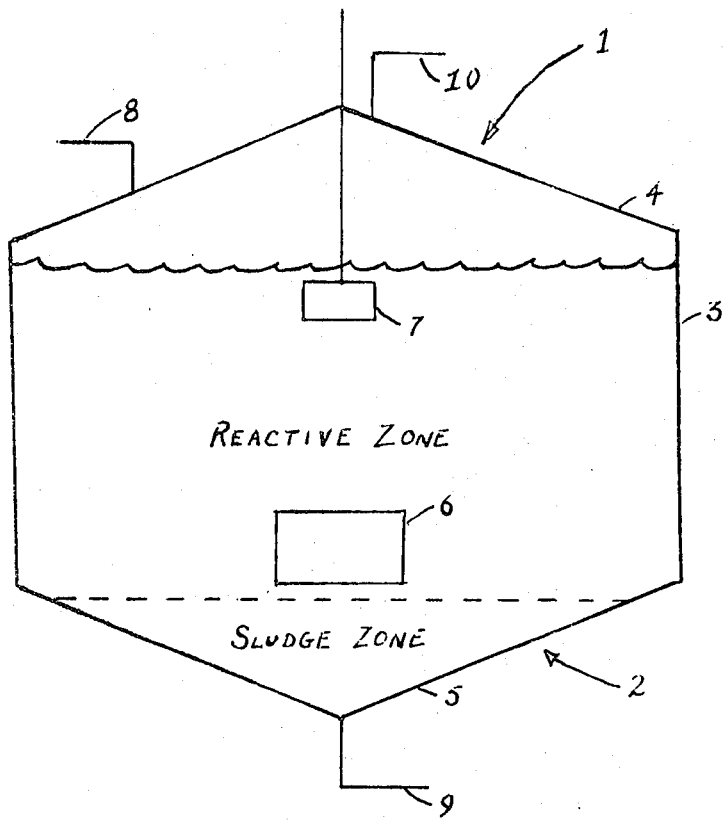
FIG. 1 is a diagrammatic cross-sectional side view of an improved bio-gas generating digester.

FIG. 1 depicts a preferred embodiment of the present invention. The digester 1 has a digester housing 2 comprising a cylindrical midsection 3 with a conical top 4 and bottom 5.

Within the digester housing 2 is a digester heater 6. Also within the digester housing 2 are magnetic field producing means 7. These magnetic field producing means are preferably a single electromagnet, but can be a series of electromagnets or a single naturally occurring magnet or a series thereof or any other means of producing a magnetic field. Although FIG. 1 shows the magnetic field producing means 7 within the digester housing 2, they may be located elsewhere, such as outside the digester housing 2, so long as they produce a magnetic field within the housing 2.

Commnicating with the interior of the digester housing 2 are an organic wastes slurry line 8, an organic wastes sludge line 9 and a bio-gas collection line 10.

In practice, a slurry of organic wastes is continuously fed to the digester 1 via organic wastes slurry line 8. The organic wastes are fermented in the digester 1 to produce bio-gas which is removed as it is formed from the digester 1 via bio-gas collection line 10. Simultaneously, organic wastes sludge is formed and extracted from digester 1 via organic wastes sludge line 9.

The digester is heated by digester heater 6 to facilitate fermentation of the organic wastes to produce the bio-gas product. To further facilitate such fermentation, bacteria are added to the organic wastes. This may either be done shortly before the organic wastes slurry is introduced into the digester 1 or thereafter. The bacteria are magnetotactic in nature and respond to a magnetic field created within the digester 1 by magnetic field producing means 7. Depending upon the polarity of the magnetic field produced and the polarity of the magnetotactic bacteria, the bacteria will migrate either toward or away from the magnetic field producing means 7. In this case, a magnetic field is chosen such that the bacteria will migrate toward the magnetic field producing means 7 and away from the point where organic wastes sludge collect to be withdrawn from the digester 1. This situates most, if not all, of the bacteria in the reactive zone and away from the sludge zone of the digester 1. The reactive and sludge zones are shown generally in FIG. 1, the reactive zone being simply the area of the digester 1 where most, if not all, of the fermentation reaction takes place and the sludge zone being simply the area of the digester 1 where organic wastes sludge collects and very little, if any, fermentation reaction occurs.

By situating the magnetotactic bacteria in the manner just described, the loss of bacteria from the digester 1 is prevented and the bacteria are located where they can work productively from a fermentation standpoint, both of which allow for an increased flow of material through the digester 1 and a more efficient process overall.

It is to be understood that the present invention is not limited to that precisely as described hereinabove. Many modifications and variations of this invention will be apparent to those skilled in the art. It is, therefore, intended that the scope of the invention be solely limited by the claims appended hereto.

I claim:

1. In a process for producing bio-gas by continuously introducing organic wastes into a digester, collecting bio-gas from the digester as it is produced by the fermentation of the organic wastes and continuously withdrawing sludge from the digester, the improvement comprising:

(a) introducing magnetotactic bacteria into the digester in an amount sufficient to facilitate the fermentation of said organic wastes; and
   (b) prohibiting said bacteria from exiting said digester with the sludge withdrawn therefrom by creating a magnetic field in said digester to situate said bacteria apart from said sludge, whereby said bacteria is retained in said digester as said sludge is being withdrawn.

2. The process of claim 1 in which the improvement further comprises creating the magnetic field by use of an electromagnet.

3. The process of claim 1 in which the improvement further comprises creating the magnetic field by use of a naturally occurring magnet.

4. In a process for producing bio-gas by continuously introducing organic wastes into a digester having a reactive zone and a sludge zone collecting bio-gas from the digester as it is produced by the fermentation of the organic wastes and continuously withdrawing sludge from the digester, the improvement comprising:

(a) introducing magnetotactic bacteria into the digester in an amount sufficient to facilitate the fermentation of said organic wastes; and
   (b) creating a magnetic field in said digester to hold said bacteria in the reactive zone of the digester.

5. The process of claim 4 in which the improvement further comprises creating the magnetic field by use of an electromagnet.

6. The process of claim 4 in which the improvement further comprises creating the magnetic field by use of a naturally occurring magnet.

* * * * *